US012742016B2

(12) United States Patent
Xu et al.

(10) Patent No.: US 12,742,016 B2
(45) Date of Patent: Sep. 22, 2026

(54) POLYPEPTIDE THAT SPECIFICALLY BINDING TO CD123 PROTEIN, POLYPEPTIDE COMPLEX, CO-DELIVERY SYSTEM AND PREPARATION METHOD AND USE THEREOF

(71) Applicants: Institute of Basic Medical Sciences Chinese Academy of Medical Sciences, Beijing (CN); National Center for Nanoscience and Technology, Beijing (CN)

(72) Inventors: Haiyan Xu, Beijing (CN); Chen Wang, Beijing (CN); Shilin Xu, Beijing (CN); Yanlian Yang, Beijing (CN); Jie Meng, Beijing (CN); Jian Liu, Beijing (CN); Tao Wen, Beijing (CN)

(73) Assignees: Institute of Basic Medical Sciences Chinese Academy of Medical Sciences, Beijing (CN); National Center for Nanoscience and Technology, Beijing (CN)

( * ) Notice: Subject to any disclaimer, the term of this patent is extended or adjusted under 35 U.S.C. 154(b) by 943 days.

(21) Appl. No.: 18/012,040

(22) PCT Filed: Jun. 22, 2021

(86) PCT No.: PCT/CN2021/101405

§ 371 (c)(1),
(2) Date: Dec. 21, 2022

(87) PCT Pub. No.: WO2021/259226

PCT Pub. Date: Dec. 30, 2021

(65) Prior Publication Data

US 2023/0250183 A1 Aug. 10, 2023

(30) Foreign Application Priority Data

Jun. 22, 2020 (CN) ......................... 202010571978.9

(51) Int. Cl.

*C07K 16/28* (2006.01)
*A61K 31/4745* (2006.01)
*A61K 31/475* (2006.01)
*A61K 31/675* (2006.01)
*A61K 31/704* (2006.01)
*A61K 38/16* (2006.01)
*A61P 35/02* (2006.01)

(52) U.S. Cl.

CPC ...... *C07K 16/2896* (2013.01); *A61K 31/4745* (2013.01); *A61K 31/475* (2013.01); *A61K 31/675* (2013.01); *A61K 31/704* (2013.01); *A61K 38/16* (2013.01); *A61P 35/02* (2018.01)

(58) Field of Classification Search

None
See application file for complete search history.

(56) References Cited

FOREIGN PATENT DOCUMENTS

| | | | |
|---|---|---|---|
| CN | 107326028 | A | 11/2017 |
| CN | 107921090 | A | 4/2018 |
| CN | 111732635 | A | 10/2020 |

OTHER PUBLICATIONS

Britannica, "Polymer", available online at https://www.britannica.com/science/macromolecule, 6 pages (accessed on Nov. 24, 25) (Year: 2025).*
Britannica, "Macromolecule", available online at https://www.britannica.com/science/macromolecule, 1 page (accessed on Nov. 24, 25) (Year: 2025).*
Testa et al., Cancers 11:31 pages (2019) (Year: 2019).*
Patnaik et al., Leukemia & Lymphoma 62:2568-2586 (2021) (Year: 2021).*
International Search Report dated Sep. 23, 2021 issued in PCT/CN2021/101405.
Wu, Haibin et al., "Novel CD123-aptamer-originated targeted drug trains for selectively delivering cytotoxic agent to tumor cells in acute myeloid leukemia theranostics", Drug Delivery (2017), vol. 24, No. 1, pp. 1216-1229.
Weng, Meng et al., "SS30, a novel thioaptamer targeting CD123, inhibits the growth of acute myeloid leukemia cells", Life Sciences (2019), vol. 232, 116663, pp. 1-12.

* cited by examiner

*Primary Examiner* — Thea D'Ambrosio
(74) *Attorney, Agent, or Firm* — Scully, Scott, Murphy & Presser, P.C.

(57) ABSTRACT

The invention discloses a polypeptide that specifically binding to CD123 protein, a polypeptide complex and a co-delivery system, and preparation methods and use thereof. The general formula of amino acid arrangement in the polypeptide is $X_1$-DYDTR-$X_2$-QGTD-$X_3$-G-$X_4$-DFR-RISD-$X_5$; it can bind to CD123-positive cells and inhibit the progression of leukemia; the polypeptide complex can increase the binding quantity of the polypeptide to CD123-positive cells, and drug can inhibit the progression of leukemia alone and prolong the survival of leukemia mice; the co-delivery system can load chemotherapy drugs for tumor treatment and reduce the toxicity of chemotherapy drugs to normal cells.

20 Claims, 5 Drawing Sheets
(2 of 5 Drawing Sheet(s) Filed in Color)

Specification includes a Sequence Listing.

POLYPEPTIDE THAT SPECIFICALLY BINDING TO CD123 PROTEIN, POLYPEPTIDE COMPLEX, CO-DELIVERY SYSTEM AND PREPARATION METHOD AND USE THEREOF

TECHNICAL FIELD

The invention relates to the technical field of biomedicine, in particular to a polypeptide that specifically binds to CD123 protein, a polypeptide complex formed by the polypeptide and a macromolecular material, a co-delivery system containing the polypeptide complex, and preparation method and use of the polypeptide, the polypeptide complex and the co-delivery system.

INCORPORATION BY REFERENCE OF SEQUENCE LISTING

The sequence listing in ASCII text format, named as 41676_SequenceListing.txt of 40,976 bytes, created on Aug. 12, 2025, and submitted to the United States Patent and Trademark Office via Patent Center, is incorporated herein by reference.

BACKGROUND

Acute myeloid leukemia (AML) is a common malignant blood tumor, accounting for about 70% of Acute leukemia. AML is characterized by abnormal proliferation and differentiation of immature myeloid cells infiltrating into bone marrow and inhibiting normal hematopoietic function of bone marrow. The therapeutic effect of targeted drugs is limited due to a large number of mutant genes involved in the disease, thus chemotherapy is still the main treatment of the disease.

The current AML chemotherapy mostly adopts the combination chemotherapy scheme based on cytarabine, and the complete response rate (the bone marrow samples of patients are tested after treatment, in which the proportion of leukemia cells is less than 5% means complete response) is about 70%. However, chemotherapy drugs can cause AML cells to up-regulate the expression of some surface proteins, reduce the sensitivity of cells to chemotherapy drugs, and also guide cells to chemotactically homing to tissues and organs with abundant stromal cells at the same time, such as bone marrow and spleen, forming minimal residual lesions in these tissues. It is thus clear that chemotherapy drugs will lead to drug resistance and recurrence (the recurrence rate of patients within three years after complete response is as high as 50%-70%), making the prognosis of AML poor (meaning that the possibility of patients being cured is very low).

In addition, chemotherapy drugs are generally lack of targeting, which will bring serious side effects. Elderly patients have a particularly poor tolerance to chemotherapy. At present, the five-year overall survival rate of AML is only about 25% (the survival rate of elderly patients is even lower than 10%). Therefore, the treatment of AML has been facing major challenges, and it is urgent to develop more effective new technologies and new treatment methods.

Studies has found that CD123 is low or no expression in normal primitive hematopoietic cells and erythroid progenitor cells. Although the expression of CD123 is relatively high in bone marrow cells and B-lymphoid progenitor cells, the expression of CD123 on the surface of bone marrow cells and B-lymphoid progenitor cells gradually decreases with the maturation of these cells. When bone marrow cells and B lymphoid progenitor cells fully mature into granulocytes and B lymphocytes respectively, CD123 is not detected in granulocytes and B lymphocytes. However, CD123 is highly expressed on the surface of leukemic stem cells and most leukemic cells, and is closely related to the poor prognosis of AML. CD123 is not only expressed in AML, but also in other blood tumors such as acute B-lymphocyte leukemia, chronic myelocytic leukemia, plasmacytoid dendritic cell neoplasm and hairy cell leukemia. It is clear that CD123 is an important target protein for leukemia treatment.

CD123 is a receptor of interleukin 3 (IL-3) and when it binds to IL-3, AML cells are activated to proliferate. Therefore, preventing the interaction between CD123 and IL-3 is the key to inhibit the proliferation of leukemia cells and induce their apoptosis. At present, anti-CD123 antibodies and antibody drugs have been reported, for example, 7G3, which belongs to mouse derived anti-CD123 monoclonal antibody (MAb), can bind to CD123 on the cell surface to prevent the interaction between CD123 and IL-3, which inhibits the proliferation of IL-3-mediated leukemia cells, and makes leukemia cells lose their activity and die. Another example is CSL362, a humanized monoclonal antibody of mouse monoclonal antibody (MAb 7G3), which can specifically recognize CD123 and block the response of AML cells to IL-3, so that leukemia cells lose their activity and die. For example, SL-401 (Tagraxofusp) is a cytotoxic targeting CD123, which is formed by recombination and fusion of human IL-3 and truncated diphtheria toxin (DT), and can effectively inhibit the proliferation of leukemia cells. For example, SL-101 is an antibody conjugate prepared by fusing anti-CD123 single chain Fv (scFv) to *Pseudomonas* exotoxin A, which can block the signaling pathway mediated by IL-3 and induce apoptosis of leukemia cells. Among the above compounds, only SL-401 was approved by the US FDA as the first CD123-targeted therapeutic drug, which is mainly used for the treatment of plasmacytoid dendritic cell neoplasm. The other drugs are in the clinical trial stage (Phase I/Phase II), and no outstanding efficacy has been observed in clinical practice.

Therefore, it is necessary to develop new CD123 antagonists.

SUMMARY OF THE INVENTION

The invention aims to solve the technical defects in the prior art. In a first aspect, provided is a chemically synthesized polypeptide with the general formula of amino acid arrangement of $X_1$-DYDTRX$_2$-QGTD-X$_3$-G-X$_4$-DFR-RISD-X$_5$ (SEQ ID NO: 1); wherein:

$X_1$ is absent, or amino acid D, or peptide fragment whose amino acid sequence is DD or GGDD (SEQ ID NO: 2);

$X_2$ is A or R;

$X_3$ is I or D;

$X_4$ is C or N;

$X_5$ is absent, or amino acid D, or peptide fragment whose amino acid sequence is DD or DRR.

It is a polypeptide fragment containing any of the following amino acids arrangement:

```
                                  (SEQ ID NO: 3)
DYDTRAQGTDIGCDFRRISD,

                                  (SEQ ID NO: 4)
DYDTRAQGTDDGCDFRRISD,
```

-continued

```
(SEQ ID NO: 5)
DYDTRRQGTDDGCDFRRISDD,

(SEQ ID NO: 6)
DDYDTRAQGTDIGCDFRRISDD,

(SEQ ID NO: 7)
DDDYDTRAQGTDIGCDFRRISDDD,

(SEQ ID NO: 8)
GGDDDYDTRAQGTDIGNDFRRISDDD,

(SEQ ID NO: 9)
DYDTRAQGTDIGCDFRRISDDRR.
```

The above polypeptides are synthesized by standard solid phase peptide synthesis.

In a second aspect, the invention provides a polypeptide complex, which is obtained by combining the polypeptide with a macromolecular material capable of loading a larger amount of polypeptides. The polypeptide complex is prepared from raw materials including 1 part by weight of the polypeptide above and 1-50 parts by weight of the macromolecular material.

Preferably, the macromolecular material is a high polymer, and the polypeptide is preferably DDDYDTRAQGTDIGCDFRRISDDD (SEQ ID NO: 7) or GGDDDYDTRAQGTDIGNDFRRISDDD (SEQ ID NO: 8).

More preferably, the average hydrodynamic diameter of the polypeptide complex is 50-150 nm.

The macromolecular material is selected from one or more of the following substances: methoxy polyethylene glycol (mPEG)—polycaprolactone (PCL) (mPEG-PCL), distearoyl phosphatidylethanolamine (DSPE)—polyethylene glycol 2000 (PEG2000) (DSPE-PEG2000), polyvinyl caprolactam—polyvinyl acetate—polyethylene glycol (Soluplus), polyoxyethylene polyoxypropylene ether block copolymer (molecular weight ratio of polyoxyethylene and polyoxypropylene is 80:20) and Polylactic acid—glycolic acid copolymer (PLGA, molecular weight ratio of polylactic acid and glycolic acid is 50:50), preferably is methoxy polyethylene glycol (mPEG)—polycaprolactone (PCL) ($mPEG_{2000}$-$PCL_{2000}$), Soluplus (molecular weight ratio of polyvinyl caprolactam, polyvinyl acetate and polyethylene glycol is 57:30:13), distearoyl phosphatidylethanolamine (DSPE)—polyethylene glycol 2000 (PEG2000) (DSPE-PEG2000).

The polypeptide complex is prepared from raw materials including polypeptide DDDYDTRAQGTDIGCDFRRISDDD (SEQ ID NO: 7) or GGDDDYDTRAQGTDIGNDFRRISDDD (SEQ ID NO: 8) and methoxy polyethylene glycol (mPEG)—polycaprolactone (PCL) ($mPEG_{2000}$-$PCL_{2000}$) or Soluplus (molecular weight ratio of polyvinyl caprolactam, polyvinyl acetate and polyethylene glycol is 57:30:13).

The invention provides a method for preparing the above polypeptide complex. Dissolving the macromolecular material and the polypeptide in PBS solution, and making them react at 25-75° C. for 20-120 min, so that the macromolecular material and the polypeptide form a complex; placing the complex at room temperature until it is clear and transparent, and filtering to remove free polypeptides (for example, using a hydrophilic polyethersulfone (PES) membrane filter), to obtain the polypeptide complex.

Preferably, the loading rate of the polypeptide in the polypeptide complex is 60-100%.

In a third aspect, the invention provides a co-delivery system, which is prepared by mixing components including the polypeptide complex and a chemotherapy drug; the chemotherapy drug is selected from one or more of vincristine, doxorubicin hydrochloride, camptothecin, cyclophosphamide, etc., preferably doxorubicin hydrochloride.

The mass ratio of the chemotherapy drug to the polypeptide complex is 1: (10-80).

The invention provides a method for preparing the co-delivery system. Dissolving the chemotherapy drug in water to obtain a stock solution of the chemotherapy drug (preferably with a concentration of 1-10 mg/mL); mixing the polypeptide complex above with the stock solution of the chemotherapy drug at 25-75° C. for 20-120 min to form a mixture, placing the mixture at room temperature, and filtering (for example, using a hydrophilic PES membrane filter) to remove free chemotherapy drug, to obtain the co-delivery system.

In a fourth aspect, the invention provides use of the polypeptide, the polypeptide complex and the co-delivery system above in the preparation of medicine for treatment of leukemia. Leukemia may be acute myeloid leukemia, acute lymphoid leukemia and chronic lymphoid leukemia.

Compared with antibodies, the polypeptide obtained by chemical synthesis in the invention has the advantages of high flexibility in sequence design, easy synthesis and modification, relatively low cost, low immunogenicity, etc. Experiments show that the polypeptide provided in the invention has weak binding to CD123-negative cells and strong binding to CD123-positive cells at the same polypeptide concentration, indicating that the polypeptide has the function of targeting CD123-positive cells, that is, the polypeptide can specifically bind to CD123-positive cells with high affinity; it is also confirmed that the affinity is concentration-dependent. At the same time, by antagonizing CD123, the polypeptide can also effectively inhibit the interaction between CD123 and IL-3 and inhibit the activation and proliferation of cells of leukemia mediated by IL-3. The polypeptide complex provided in the invention is a micellar polypeptide complex formed by combining the polypeptide with the macromolecular material. The experiment proves that the polypeptide complex can load polypeptides. Compared with the polypeptide alone, the binding quantity of the polypeptide complex to CD123-positive cells is increased, thus better inhibiting the activity of leukemia cells. In the treatment experiment on leukemia-bearing animals, the polypeptide complex of the invention can significantly prolong the survival of acute myeloid leukemia-bearing mice and has therapeutic effect. The invention also loads chemotherapy drugs on the polypeptide complex, forming a co-delivery system of polypeptides and chemotherapy drugs that antagonize CD123. Experiments show that the co-delivery system can significantly enhance the killing activity of chemotherapy drugs to CD123-positive cells, while reducing the toxicity of chemotherapy drugs to normal cells (see Experiment 9), indicating that the co-delivery system provided in the invention will have more significant advantages in the use of targeted therapy for tumors.

The polypeptide, polypeptide complex and co-delivery system targeting CD123 provided in the invention can provide a feasible treatment strategy for the treatment of leukemia, and has broad prospects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
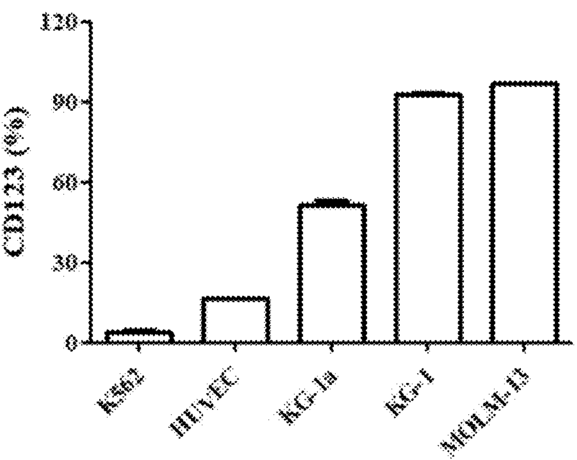
FIG. 1 depicts the expression level histogram of CD123 protein in CD123-positive leukemia cell lines (MOLM-13, KG-1a, KG-1), CD123-negative leukemia cell line K562 cells and primary human umbilical vein endothelial cells (HUVEC)

Since the development of polypeptide drugs targeting CD123 is of great significance for the effective treatment of leukemia, and there is no literature report on polypeptides targeting and antagonizing CD123. The present application provides a kind of polypeptide targeting CD123, its general formula of amino acid arrangement is $X_1$-DYDTR-$X_2$-QGTD-$X_3$-G-$X_4$-DFRRISD-$X_5$ (SEQ ID NO: 1), wherein $X_1$ is absent, or amino acid D, or peptide fragment whose amino acid sequence is DD or GGDD (SEQ ID NO: 2); $X_2$ is A or R; $X_3$ is I or D; $X_4$ is C or N; $X_5$ is absent or amino acid D or peptide fragment whose amino acid sequence is DD or DRR; in the general formula, D represents Asp (aspartic acid), Y represents Tyr (tyrosine), T represents Thr (threonine), R represents Arg (arginine), Q represents Gln (glutamine), G represents Gly (glycine), F represents Phe (phenylalanine), I represents Ile (isoleucine), S represents Ser (serine), C represents Cys (cysteine), and N represents Asn (asparagine).

Based on the above polypeptides (unless otherwise specified below, the mentioned polypeptides are all polypeptides targeting CD123 provided in the present application), the present application also provides a polypeptide complex. Based on the above polypeptide complex, the present application also provides a co-delivery system.

The contents of the invention are explained in more detail and the invention is further elaborated in combination with specific examples as follows, but these examples are by no way of limitation of the invention.

The embodiments of the invention will be described in detail below in combination with examples. Where the specific technology or conditions are not specified in the examples, they shall be carried out in accordance with the technology or conditions described in the literature in the field or in accordance with the product specification.

The reagents or instruments used that do not indicate the manufacturer are conventional products that can be purchased through proper channels.

The cell lines used in the following examples are purchased from the National Infrastructure of Cell Line Resource; MOLM-13, KG-1a and KG-1 cells used are all from the Blood Diseases Hospital of the Chinese Academy of Medical Sciences, unless otherwise specified.

The solvents of the aqueous solutions in the following examples are sterile ultra-pure water solutions, unless otherwise specified.

The reagents used in the following examples are analytically pure reagents, unless otherwise specified.

The phosphate buffer used in the following examples is 1×PBS solution (pH=7.4), unless otherwise specified.

Example 1: Polypeptide and Preparation Thereof

Polypeptides targeting CD123, whose amino acid sequences are shown in Table 1, were prepared by standard solid phase peptide synthesis. They were all white powder with purity ≥98%. In order to verify the effect of the polypeptides, the polypeptides shown in Table 1 were prepared into stock solutions of the polypeptides with a concentration of 1 mM with PBS buffer solution before all experiments.

TABLE 1

Amino acid sequence of polypeptide

| NO | Name | Sequence |
|---|---|---|
| 1# | PO-4 | DYDTRAQGTDIGCDFRRISD (SEQ ID NO: 3) |
| 2# | PO-4-1 | DYDTRAQGTDDGCDFRRISD (SEQ ID NO: 4) |
| 3# | PO-4-2 | DYDTRRQGTDDGCDFRRISDD (SEQ ID NO: 5) |
| 4# | PO-5 | DDYDTRAQGTDIGCDFRRISDD (SEQ ID NO: 6) |
| 5# | PO-6 | DDDYDTRAQGTDIGCDFRRISDDD (SEQ ID NO: 7) |

TABLE 1-continued

| Amino acid sequence of polypeptide | | |
|---|---|---|
| NO | Name | Sequence |
| 6# | PO-6N | GGDDDYDTRAQGTDIGNDFRRISDDD (SEQ ID NO: 8) |
| 7# | PO-7 | DYDTRAQGTDIGCDFRRISDDRR (SEQ ID NO: 9) |

The polypeptides in Table 1 were identified as target polypeptides by HPLC and MS.

Example 2: Polypeptide Complex and Preparation Thereof

The preparation method of polypeptide complex comprises the following steps:

(1) 1-50 mg of high polymer and 1 mg of polypeptide were dissolved in PBS solution, and Solution A was obtained through ultrasonic vortex dissolution; the high polymer was selected from one or more of methoxy polyethylene glycol (mPEG)—polycaprolactone (PCL) ($mPEG_{2000}$-$PCL_{2000}$), distearoyl phosphatidylethanolamine (DSPE)—polyethylene glycol 2000 (PEG2000) (DSPE-PEG2000), polyvinyl caprolactam—polyvinyl acetate—polyethylene glycol (Soluplus), polyoxyethylene polyoxypropylene ether block copolymer (molecular weight ratio of polyoxyethylene and polyoxypropylene is 80:20), polylactic acid—glycolic acid copolymer (PLGA, molecular weight ratio of polylactic acid and glycolic acid is 50:50), preferably methoxy polyethylene glycol (mPEG)—polycaprolactone (PCL) ($mPEG_{2000}$-$PCL_{2000}$, commercially available), Soluplus (commercially available, molecular weight ratio of polyvinyl caprolactam, polyvinyl acetate and polyethylene glycol is 57:30:13), distearoyl phosphatidylethanolamine (DSPE)—polyethylene glycol 2000 (PEG2000) (DSPE-PEG2000).

(2) Solution B was obtained by reacting Solution A in a constant temperature water bath at 25-75° C. for 20-120 min.

(3) Solution B was placed at room temperature for 1-2 hours until it was clear and transparent. The free polypeptides were removed by filtration with a hydrophilic PES membrane filter of 0.22 m. Polypeptide complex was contained in the collected filtrate.

In the polypeptide complex prepared by this method, the polypeptide is combined with the macromolecular material to form a micellar form, and the average hydrodynamic diameter may generally vary in the range of 50-150 nm; the loading rate of polypeptide in the polypeptide complex may be 50H100%, preferably 60%-1000%, taking the percentage of the quantity of polypeptide loaded in the polypeptide complex to the quantity of polypeptide added in step (1) as the loading rate of polypeptide in the polypeptide complex.

According to the above method, a series of polypeptide complexes (represented by "C-number") were prepared from polypeptide PO-6 and polypeptide PO-6N listed in Table 1. For different polypeptide complexes, only the composition of raw materials used and preparation parameters were adjusted, as shown in Table 2 for details.

TABLE 2

Preparation Parameters of Polypeptide Complex

| Polypeptide Complex | high polymer | | Polypeptide | | Heating temperature/° C. | time/min | average hydrodynamic diameter/nm | loading rate/% |
|---|---|---|---|---|---|---|---|---|
| C-1 | $mPEG_{2000}$-$PCL_{2000}$ | 15 mg | PO-6 | 1 mg | 60 | 120 | 77 | 91 |
| C-2 | DSPE-PEG2000 | 30 mg | | 1 mg | 30 | 45 | 65 | 60 |
| C-3 | Soluplus | 10 mg | | 1 mg | 55 | 30 | 73 | 92 |
| C-4 | PLGA | 20 mg | | 1 mg | 25 | 60 | 150 | 88 |
| C-5 | polyoxyethylene polyoxypropylene ether block copolymer | 2 mg | | 2 mg | 40 | 80 | 120 | 90 |
| C-6 | $mPEG_{2000}$-$PCL_{2000}$ + PLGA | 40 mg + 40 mg | | 2 mg | 75 | 50 | 130 | 78 |
| C-1' | $mPEG_{2000}$-$PCL_{2000}$ | 23 mg | PO-6N | 1 mg | 60 | 85 | 75 | 79 |
| C-2' | DSPE-PEG2000 | 30 mg | | 1.5 mg | 25 | 60 | 82 | 65 |
| C-3' | Soluplus | 15 mg | | 1 mg | 55 | 30 | 66 | 84 |
| C-4' | PLGA | 35 mg | | 2 mg | 35 | 80 | 147 | 74 |
| C-5' | polyoxyethylene polyoxypropylene ether block copolymer | 2 mg | | 1 mg | 40 | 80 | 105 | 81 |
| C-6' | $mPEG_{2000}$-$PCL_{2000}$ + PLGA | 35 mg + 35 mg | | 1.5 mg | 70 | 50 | 128 | 68 |

Example 3: Co-Delivery System and Preparation Thereof

The preparation method of the co-delivery system comprises the following steps:

(1) Chemotherapy drug (vincristine, doxorubicin hydrochloride, camptothecin, or cyclophosphamide, etc.) was dissolved in sterile water to prepare a stock solution of the chemotherapy drug with a concentration of 1-10 mg/mL, and doxorubicin hydrochloride was preferred as the chemotherapy drug.

(2) The stock solution of the chemotherapy drug obtained in step (1) was mixed with the polypeptide complex in Example 2 according to the mass ratio of chemotherapy drug to polypeptide complex of 1: (10-80), and was mixed in a constant temperature water bath at 25-75° C.

for 20-120 min to encapsulate the chemotherapy drug in the polypeptide complex to obtain Solution D.

(3) The Solution D was placed at room temperature and filtered by a hydrophilic PES membrane filter of 0.22 m to remove free drug and the co-delivery system formed by the polypeptide complex and the chemotherapy drug was obtained with average hydrodynamic diameter of 50-200 nm.

The encapsulation rate of the chemotherapy drug in the co-delivery system refers to the percentage of the quantity of the chemotherapy drug encapsulated in the co-delivery system to the quantity of the chemotherapy drug added in step (2). The encapsulation rate of the chemotherapy drug in the co-delivery system in this example is 30-99%, preferably 40%-99%.

The use concentration of the co-delivery system in this example complies with the use requirements of various chemotherapy drugs.

According to the above method, a series of co-delivery systems consisting of polypeptide complex and chemotherapy drugs were prepared. For different co-delivery systems, only the parameters of the added chemotherapy drugs were adjusted, as shown in Table 3 for details.

TABLE 3

Parameters of chemotherapy drugs loaded

| Types of chemotherapy drugs | Polypeptide complex | Chemotherapy drug:Polypeptide complex (mass ratio) | Heating temperature/ ° C. | Time/ min | Encapsulation rate/% |
|---|---|---|---|---|---|
| vincristine | C-1 | 1:40 | 60 | 120 | 55 |
| | C-2 | 1:40 | 30 | 45 | 85 |
| | C-3 | 1:20 | 55 | 30 | 78 |
| | C-4 | 1:30 | 25 | 60 | 92 |
| | C-5 | 1:60 | 40 | 80 | 45 |
| | C-6 | 1:15 | 75 | 50 | 88 |
| doxorubicin hydrochloride | C-1 | 1:10 | 60 | 120 | 90 |
| | C-2 | 1:13 | 30 | 45 | 40 |
| | C-3 | 1:10 | 55 | 30 | 99 |
| | C-4 | 1:12 | 25 | 60 | 68 |
| | C-5 | 1:30 | 40 | 80 | 75 |
| | C-6 | 1:60 | 75 | 50 | 60 |
| camptothecin | C-1 | 1:80 | 60 | 120 | 93 |
| | C-2 | 1:10 | 30 | 45 | 88 |
| | C-3 | 1:33 | 55 | 30 | 90 |
| | C-4 | 1:20 | 25 | 60 | 58 |
| | C-5 | 2:45 | 40 | 80 | 66 |
| | C-6 | 1:60 | 75 | 50 | 85 |
| Cyclophosphamide | C-1 | 1:20 | 60 | 120 | 55 |
| | C-2 | 1:20 | 30 | 45 | 78 |
| | C-3 | 1:50 | 55 | 30 | 92 |
| | C-4 | 1:60 | 25 | 60 | 95 |
| | C-5 | 1:36 | 40 | 80 | 85 |
| | C-6 | 1:12 | 75 | 50 | 82 |

Experiment 1: Determination of CD123 Expression in MOLM-13, KG-La, KG-1, K562 and HUVEC Cells by Flow Cytometry MOLM-13, KG-1a, KG-1, K562 and HUVEC cells were collected respectively into 1.5 mL Ep tubes, washed once with PBS, centrifuged at 1500 rpm for 5 min, and the precipitates were resuspended in 100 μL PBS solution containing 0.5 wt % fetal bovine serum albumin. Then anti-human CD123 antibody (Biolegend) labeled with fluorescein isothiocyanate (FITC) was added in, with 2 μL FITC labeled anti-human CD123 antibody for each 100 μL cell suspension, incubated in dark at room temperature for 30 min. After incubation, washed once with PBS solution, centrifuged at 1500 rpm for 5 min, and the precipitates were resuspended in 100 μL PBS solution. Flow cytometry was used to detect the positive rate of cells, as shown in FIG. 1.

FIG. 1 shows that the positive rates of CD123 expression in MOLM-13 cells, KG-1 cells and KG-1a cells are all higher than 50%, belonging to the positive cells expressing CD123; the positive rates of CD123 expression in HUVEC and K562 cells are lower than 20%, belonging to CD123-negative cells.

Therefore, MOLM-13 cells, KG-1 cells and KG-1a cells were used as positive cells expressing CD123 in subsequent experiments.

Figure 2:
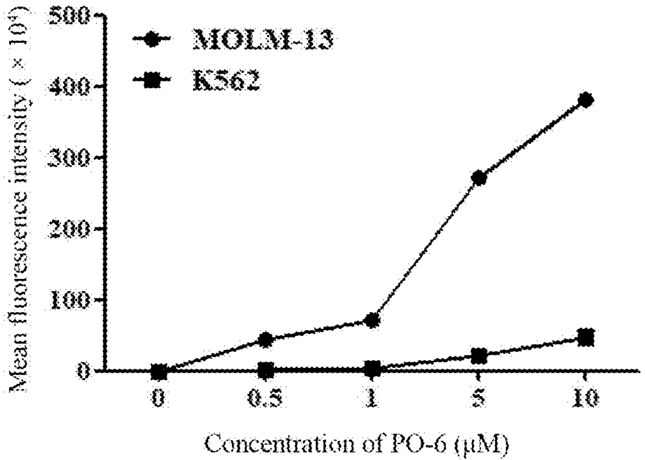
FIG. 2 depicts the curve of binding quantity of polypeptide PO-6 of the invention to MOLM-13 cells and K562 cells at different concentrations, wherein PO-6 is labeled with fluorescent molecule Fluorescein Isothiocyanate (FITC), and the binding quantity to cells is indicated by the mean fluorescence intensity of FITC of cells.
Figure 3:
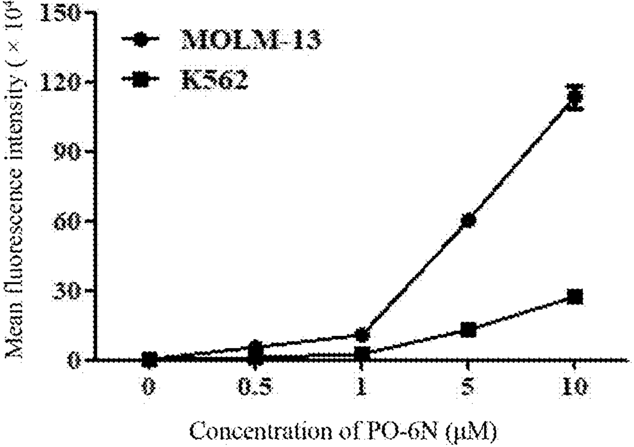
FIG. 3 depicts the curve of the binding quantity of polypeptide PO-6N of the invention to MOLM-13 cells and K562 cells at different concentrations, wherein PO-6N is labeled with fluorescent molecule FITC, and the binding quantity to cells is indicated by the mean fluorescence intensity of FITC of cells.

Experiment 2: Determination of Polypeptide Binding to MOLM-13 and K562 Cells by Flow Cytometry MOLM-13 and K562 cells were inoculated into 48-well plates with $2\times10^5$ cells per well, respectively, and FITC-labeled polypeptides listed in Table 1 were added to make the final concentrations of polypeptides were 0.5 μM, 1 μM, 5 μM and 10 μM, respectively. Incubate at 37° C. in 5% $CO_2$ incubator for 0.5 h. After incubation, washed once with PBS solution, centrifuged at 1500 rpm for 5 min, and the supernatant was discarded, and 100 μL PBS solution was added to each well to re-suspend the cells, and 300 mesh sieve was used for filtration. Flow cytometry was used for determination of the mean fluorescence intensity (MFI) of MOLM-13 and K562 cells, and MFI was used as indication of the binding quantity of polypeptide on cells. FIGS. 2 and 3 show the quantity of polypeptides bound to cells.

In FIG. 2, taking polypeptide PO-6 as an example, which shows that PO-6 can bind to CD123-positive MOLM-13 cells, and with the increase of PO-6 concentration, the mean fluorescence intensity of cells increases, indicating that the quantity of polypeptide bound on cells increases, and the binding ability is concentration-dependent. At the same concentration of PO-6, the mean fluorescence intensity on CD123-negative K562 cells is very low, and significantly lower than that of MOLM-13 cells, indicating that PO-6 can bind to CD123-positive cells, while the binding ability to CD123-negative cells is very weak. It can be seen that PO-6 has the function of targeting CD123-positive cells.

In FIG. 3, taking polypeptide PO-6N as an example, which shows that PO-6N can bind to CD123-positive MOLM-13 cells, and with the increase of concentration, the mean fluorescence intensity of cells increases, indicating that the number of polypeptides bound increases, and the binding ability is concentration-dependent. At the same concentration of PO-6N, the mean fluorescence intensity of CD123-negative K562 cells is very low, and significantly lower than that of MOLM-13 cells, indicating that the binding ability of PO-6N to CD123-negative cells is very weak.

The other polypeptides in Table 1 were consistent with the results of this experiment, that is, they can bind to CD123-positive MOLM-13 cells but weakly bind to CD123-negative K562 cells, so they are not listed in detail.

Experiment 3: Hydrodynamic Diameter Distribution of Polypeptide Complex

Polypeptide complex C-1 and co-delivery system composed of polypeptide complex C-1 and doxorubicin hydrochloride were prepared according to the preparation method of polypeptide complex and co-delivery system in Example 2 and Example 3. 1 mL of the solution of the above-mentioned co-delivery system was pipetted and placed in a cuvette, and Nano ZS90 nanoparticle analyzer was used for detection of the distribution of hydrodynamic diameters.

Figure 4:
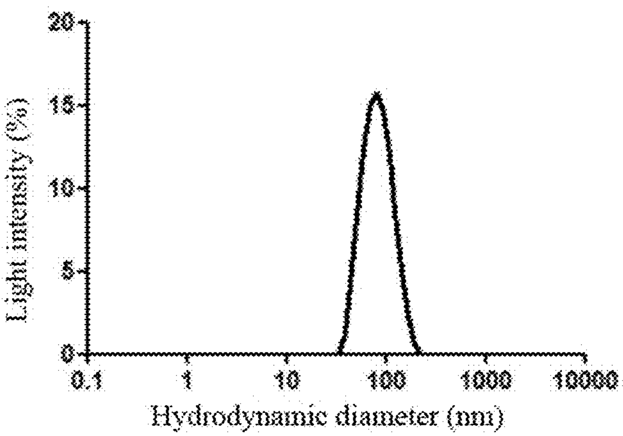
FIG. 4 is the dynamic light scattering diagram of polypeptide complex (C-1) of the invention in PBS solution.
Figure 5:
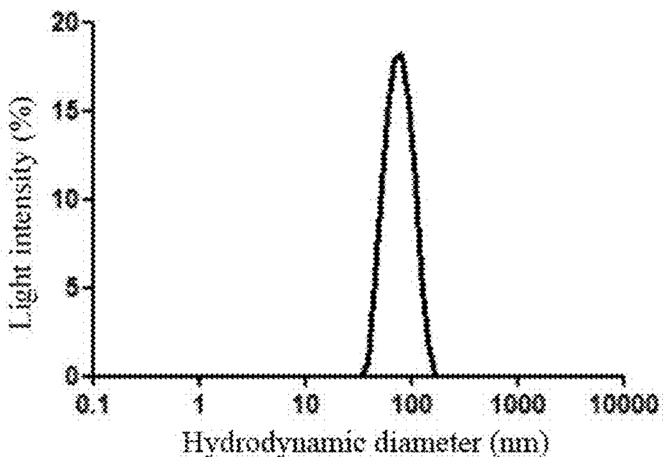
FIG. 5 is the dynamic light scattering diagram of the co-delivery system formed by the polypeptide complex (C-1) of the invention and the chemotherapy drug doxorubicin hydrochloride in PBS solution.

The results are shown in FIG. 4 and FIG. 5.

It can be seen from FIG. 4 that the average hydrodynamic diameter of polypeptide complex C-1 is about 77 nm. It can be seen from FIG. 5 that the average hydrodynamic diameter of the drug co-delivery system composed of polypeptide complex C-1 and chemotherapy drug doxorubicin hydrochloride is about 72 nm.

In FIG. 4 and FIG. 5, the particle size of polypeptide complex and drug co-delivery system is normally distributed, and the peak width is narrow, indicating that the polypeptide complex C-1, and the drug co-delivery system consisting of polypeptide complex C-1 and chemotherapy drug doxorubicin hydrochloride both have formed stable nanoparticles with uniform size. In addition, the particle size is below 100 nm, which is conducive to its nanosize effect.

This experiment was also carried out on other polypeptide complexes and co-delivery systems in Table 2 and Table 3, and similar results were obtained, so they are not described in detail.

Experiment 4: Determination of the Affinity of Polypeptide Complex to MOLM-13 Cells by Flow Cytometry MOLM-13 cells were inoculated into 48-well plates with $2\times10^5$ cells per well and FITC-labeled polypeptide complexes listed in Table 2 were added to make the final concentrations of polypeptide complexes were 0.1 μM, 0.3 μM, 0.5 μM and 1 μM, respectively. Incubated at 37° C. in 5% $CO_2$ incubator for 0.5 h, then washed once with PBS solution, centrifuged at 1500 rpm for 5 min, and the supernatant was discarded, and 100 μL PBS solution was added to each well to re-suspend the cells, and 300 mesh sieve was used for filtration. Since the polypeptide complex has green fluorescence, if the cell gets green fluorescence, it means that the polypeptide complex has been bound to the cell. Flow cytometry was used to detect the mean fluorescence intensity (MFI) of the cell, and MFI represents the binding quantity of polypeptide on the cell.

Figure 6:
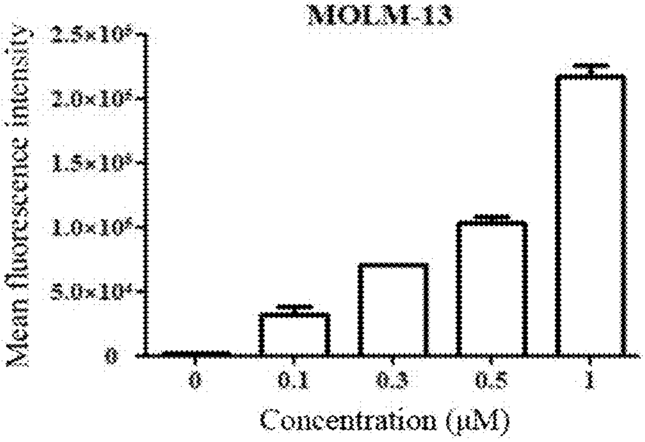
FIG. 6 is the histogram of the binding quantity of the polypeptide complex (C-1) of the invention to MOLM-13 cells, wherein the polypeptide complex is labeled with fluorescent molecule FITC, and the binding quantity to cells is indicated by the mean fluorescence intensity of FITC of cells.

Taking polypeptide complex C-1 as an example, the results are shown in FIG. 6.

FIG. 6 shows that polypeptide complex C-1 can bind to MOLM-13 cells, and with the increase of polypeptide concentration, the mean fluorescence intensity of cells increases in a concentration-dependent manner; it indicates that polypeptide complex C-1 has the function of targeting CD123-positive cells, MOLM-13.

Other polypeptide complexes in Table 2 were the same as the results of this experiment, that is, they can bind to MOLM-13 cells, and with the increase of polypeptide concentration, the mean fluorescence intensity of cells increases, which is concentration-dependent, so they are not listed in detail.

Experiment 5: Determination of the Affinity of Polypeptide Complex to KG-1a Cells by Flow Cytometry As in experiment 4, only the MOLM-13 cells in experiment 3 were replaced with KG-1a cells. Taking polypeptide complex C-3 as an example, the results are shown in FIG. 7.

Figure 7:
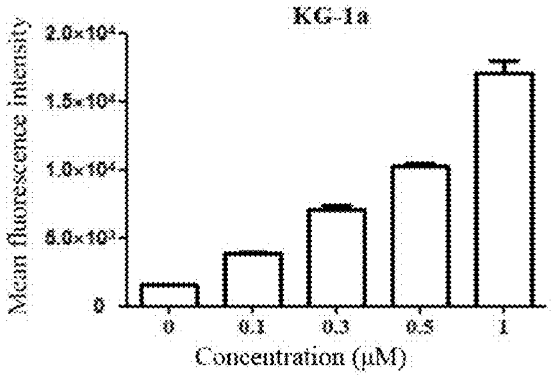
FIG. 7 is the histogram of the binding quantity of the polypeptide complex (C-1) of the invention to KG-1a cells, wherein the polypeptide complex is labeled with fluorescent molecule, FITC, and the binding quantity to cells is indicated by the mean fluorescence intensity of FITC of cells.

FIG. 7 shows that polypeptide complex C-3 can effectively bind to KG-1a cells, and with the increase of polypeptide concentration, the mean fluorescence intensity of cells increases in a concentration-dependent manner; it indicates that polypeptide complex C-3 has the ability to target CD123-positive cells, KG-1a.

Other polypeptide complexes in Table 2 were the same as the results of this experiment, that is, they can bind to KG-1a cells, and with the increase of polypeptide concentration, the mean fluorescence intensity of cells increases, which is concentration-dependent, so they are not listed in detail.

Experiment 6: Determination of the Affinity of Polypeptide Complex to KG-1 Cells by Flow Cytometry As in experiment 4, only the MOLM-13 cells in experiment 3 were replaced with KG-1 cells. Taking polypeptide complex C-1' as an example, the results are shown in FIG. 8.

Figure 8:
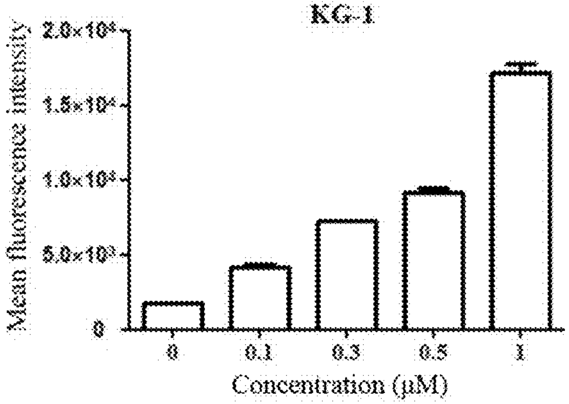
FIG. 8 is the histogram of the binding quantity of the polypeptide complex (C-1) of the invention to KG-1 cells, wherein the polypeptide complex is labeled with fluorescent molecule, FITC, and the binding quantity to cells is indicated by the mean fluorescence intensity of FITC of cells.

FIG. 8 shows that polypeptide complex C-1' can effectively bind to KG-1 cells, and with the increase of polypeptide concentration, the mean fluorescence intensity of cells increases in a concentration-dependent manner; it indicates that polypeptide complex C-1' has the ability to target CD123-positive cells, KG-1.

Other polypeptide complexes in Table 2 were the same as the results of this experiment, that is, they can bind to KG-1 cells, and with the increase of polypeptide concentration, the mean fluorescence intensity of cells increases, which is concentration dependent, so they are not listed in detail.

Experiment 7: Binding of Polypeptide, Polypeptide Complex to MOLM-13 Observed by Laser Scanning Confocal Microscope MOLM-13 cells ($2\times10^5$ cells per well) were incubated with FITC-labeled polypeptides (taking PO-6, and PO-6N as examples) and polypeptide complexes (see Table 2) at 37° C. for 30 min, and the final concentration of polypeptides was 0.5 μM (the final concentration of polypeptides in the cultivation system of polypeptide complexes was also 0.5 μM). After incubation, the cells were collected and washed twice with PBS solution, centrifuged at 1500 rpm for 5 min, and the supernatant was discarded. 400 μL paraformaldehyde in PBS aqueous solution (containing 4 wt % paraformaldehyde) was added to each well, and they were placed in dark at room temperature for 30 min, so that the cells were fixed by paraformaldehyde. washed once with PBS solution, centrifugated at 2000 rpm for 5 min, and the cells were dropped on the glass slide to dry naturally, and then was sealed with a mounting medium containing DAPI (4', 6-diamidino-2-phenylindole). Laser scanning confocal microscope (Ex=488 nm (FITC); Ex=405 nm (DAPI)) was used for observation and photographing. MOLM-13 cells without any treatment were taken as the control group, i.e., Con. Photos of polypeptide PO-6 and PO-6N and corresponding polypeptide complexes (taking C-1 and C-1' as examples) are shown in FIG. 9 and FIG. 10.

Figure 9:
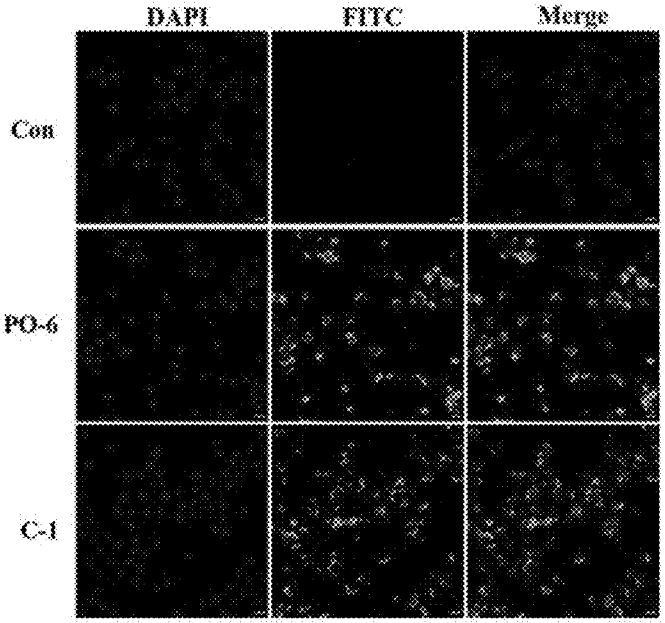
FIG. 9 shows the distribution picture of polypeptide PO-6 and polypeptide complex (C-1) of the invention on MOLM-13 cells (scale: 10 m)
Figure 10:
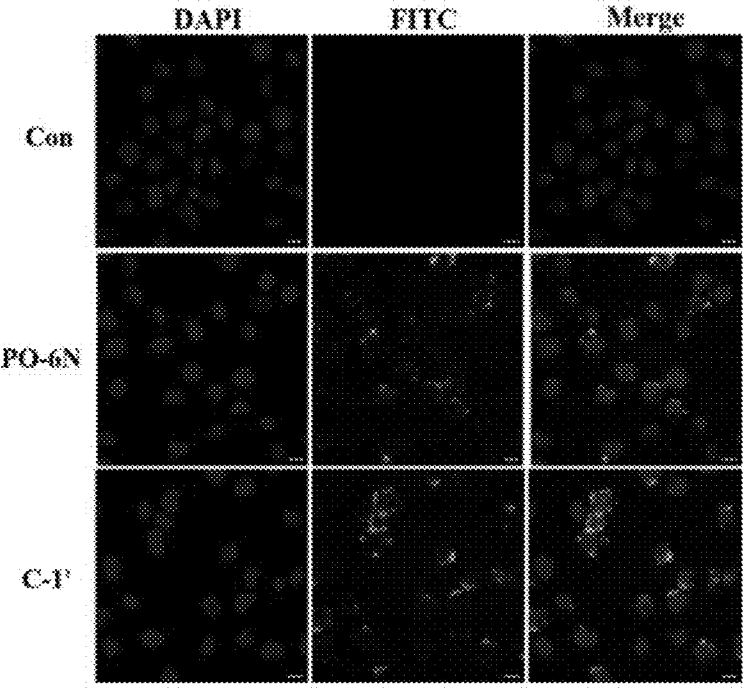
FIG. 10 shows the distribution picture of polypeptide PO-6N and polypeptide complex (C-1') of the invention on MOLM-13 cells (scale: 10 m)

In FIG. 9 and FIG. 10, FITC indicates polypeptide, DAPI indicates nucleus, and Merge indicates the effect picture after superposition of FITC and DAPI.

FIG. 9 shows that, compared with Con, obvious green fluorescence on the cell surface can be observed for FITC-labeled PO-6 and polypeptide complex C-1 after incubating with MOLM-13 cells for 0.5 h, and the fluorescence on the cell surface for C-1 after incubation is significantly stronger than that for PO-6, indicating that both PO-6 and polypeptide complex C-1 both have the function of specifically targeting and binding to MOLM-13 cells, and the binding function of C-1 is stronger.

FIG. 10 shows that, compared with Con, obvious green fluorescence on the cell surface can be observed for FITC-labeled PO-6N and polypeptide complex C-1' after incubating with MOLM-13 cells for 0.5 h, and the fluorescence on the cell surface for C-1' after incubation is significantly stronger than that for PO-6N, indicating that both PO-6N and polypeptide complex C-1' both have the function of specifically targeting and binding to MOLM-13 cells, and the binding function of C-1' is stronger.

Other polypeptide complexes (C-2-C-6, C-2'-C-6') in Table 2 were the same as the results of this experiment, that is, after incubation with MOLM-13 cells for 0.5 h, obvious green fluorescence can be observed on the cell surface, and the fluorescence of the cell surface for polypeptide complex after incubation is significantly stronger than that for the corresponding polypeptide, which are not listed in detail.

Experiment 8: Effect of Co-Delivery System on the Activity of MOLM-13 Cells

The following experimental groups were set and stock solutions for experiment were configured, including:

1) Polypeptide PO-6 group (PO-6): polypeptide stock solution obtained in Example 1 (polypeptide concentration is 1 mM);
2) Doxorubicin (Dox) group: doxorubicin hydrochloride was dissolved in sterile water to obtain 1 mg/mL (1.7 mM) Dox stock solution;
3) High polymer group ($mPEG_{2000}$-$PCL_{2000}$): 15 mg $mPEG_{2000}$-$PCL_{2000}$ powder was weighted and dissolved with 1 mL PBS solution to obtain 15 mg/mL (3.3 mM) $mPEG_{2000}$-$PCL_{2000}$ stock solution.
4) Polypeptide PO-6 and Dox combination group (PO-6+Dox): the polypeptide stock solution in experimental group 1) and the Dox stock solution in experimental group 2) were diluted with PBS solution respectively, then mixed to obtain a mixed solution. The concentration of polypeptide was 36.2 μM, the concentration of Dox was 17.24 μM, and the weight ratio of polypeptide PO-6 to Dox was 10:1 in the mixed solution;
5) Polypeptide complex group (C-1): polypeptide complex C-1 listed in Table 2 was diluted with PBS solution to a concentration of 36.2 μM of PO-6;
6) Doxorubicin micelle group (M-Dox): the Dox stock solution in experimental group 2) and the $mPEG_{2000}$-$PCL_{2000}$ stock solution in experimental group 3) were diluted with PBS solution to the concentration of $mPEG_{2000}$-$PCL_{2000}$ of 3.3 μM, and the concentration of Dox of 17.24 μM, respectively, and they were mixed based on weight ratio of $mPEG_{2000}$-$PCL_{2000}$ to Dox of 150:1.
7) Co-delivery system group (C-1-Dox): the co-delivery systems listed in Table 3 were diluted with PBS solution to the polypeptide concentration of less than 36.2 μM and the Dox concentration of less than 17.24 μM.

Experimental procedure: MOLM-13 cells were inoculated in 96-well U-shaped plates with $8\times10^4$ cells per well. Corresponding drug stock solutions were added into each well in each experimental group to make the final Dox concentration of each well is 0.1 μM and the final corresponding polypeptide concentration of each well is 0.21 μM. Incubated at 37° C. in 5% $CO_2$ incubator for 24 hours, then washed with PBS, and 110 μL CCK8 diluent (including 100 μL RPMI 1640 medium+10 μL CCK-8) was added in each well, followed by incubation for 2 h. The absorbance values (OD value) at wavelengths of 450 nm and 630 nm were measured by a microplate reader, and the percent viability of cells was calculated according to Formula 1, and the control group was the cells without drug treatment, denoted as Con; Formula 1: percent viability of cells=$OD_{450-630}$ (experimental group)/OD450-630 (control group)×100%. The results are shown in FIG. 11.

Figure 11:
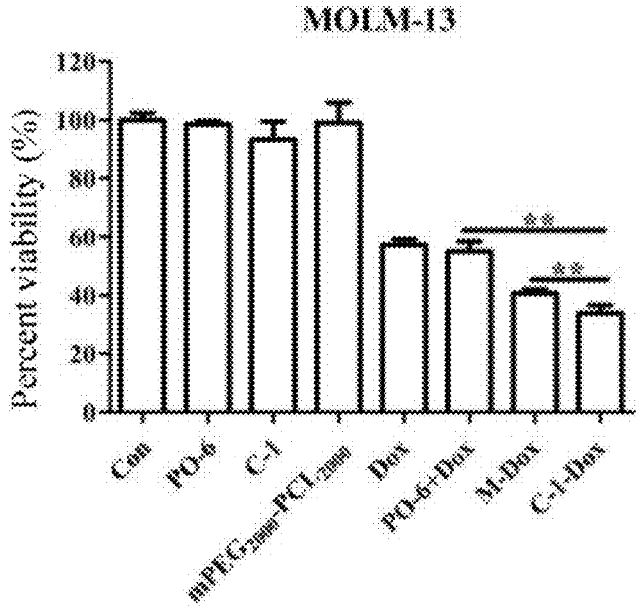
FIG. 11 is the toxicity histogram of the co-delivery system of the invention formed by the polypeptide complex (C-1) and the chemotherapy drug to MOLM-13 cells.

FIG. 11 shows that when Dox concentration in the co-delivery system is 0.1 M and PO-6 is 0.21 M, percent viability of cells of PO-6 group, Dox group, C-1 group, M-dox group, PO-6+Dox group and C-1-Dox group are 98%, 57%, 93%, 38%, 55% and 34%, respectively.

These results show that, compared with PO-6 group, Dox group, C-1 group, M-Dox group and PO-6+Dox group, the co-delivery system endows Dox targeting at the same Dox concentration. Therefore, the cytotoxicity of C-1-Dox against MOLM-13 cells (percent viability of cells is 34%) is stronger than that of PO-6+Dox group (percent viability of cells is 55%) and M-Dox group (percent viability of cells is 38%), with a significant difference.

Replacing the co-delivery system group (Group 7)) in this experiment with other co-delivery systems in Table 3, the results show that, under the same concentration of each component, percent viability of cells of the co-delivery system group to MOLM-13 cells is within the range of 28-37%, which is lower than that of both PO-6+Dox group and M-Dox group.

Experiment 9: Effect of Co-Delivery System on the Activity of HUVEC Cells

HUVEC cells were inoculated in 96-well plates with $1\times10^4$ cells per well, and grouping was the same as experiment 8. Corresponding drug stock solutions were added into each well in each experimental group to make the final Dox concentration of each well is 0.1 μM and the final corresponding polypeptide concentration of each well is 2.1 μM. Incubated at 37° C. in 5% $CO_2$ incubator for 24 hours, then washed with PBS, and 110 μL CCK8 diluent (including 100 μL RPMI 1640 medium+10 μL CCK-8) was added in each well, followed by incubation for 2 h. The absorbance values (OD value) at wavelengths of 450 nm and 630 nm were measured by a microplate reader, and the percent viability of cells was calculated according to Formula 1, and the control group was the cells without drug treatment, denoted as Con. Taking polypeptide PO-6 and polypeptide complex C-1 as examples, the results are shown in FIG. 12.

Figure 12:
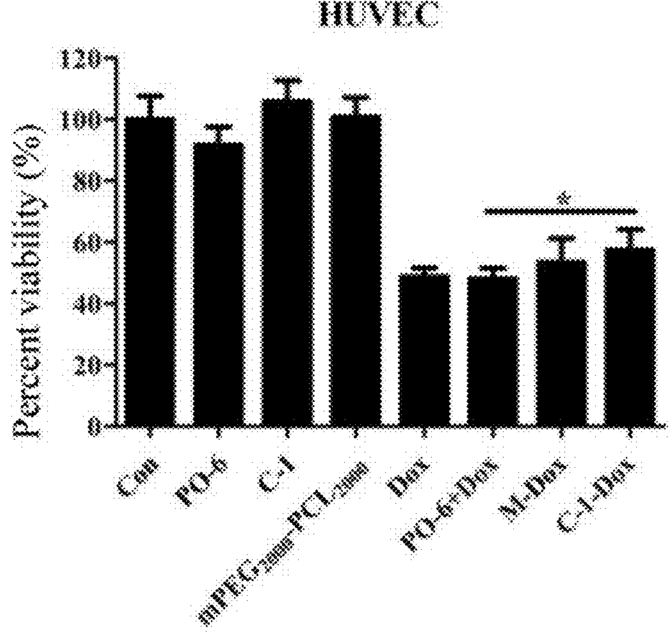
FIG. 12 is the toxicity histogram of the co-delivery system of the invention formed by the polypeptide complex (C-1) and the chemotherapy drug to HUVEC cells.

FIG. 12 shows that percent viability of cells of $mPEG_{2000}$-$PCL_{2000}$ group, PO-6 group and C-1 group is more than 90% within the tested concentration range; the percent viability of Dox, M-Dox, PO-6+Dox groups is about 50%, while percent viability of cells of C-1-Dox group is about 60%, which indicates that the targeting of C-1-Dox to CD123 does not increase the toxicity of Dox to HUVEC cells, but decreases, which indirectly indicates that the binding ability of PO-6 to HUVEC cells with low expression of CD123 is low, which is conducive to reducing the killing activity of Dox to normal cells.

Replacing the co-delivery system group (Group 7)) in this experiment with other co-delivery systems in Table 3, the results show that, under the same concentration of each component, percent viability of cells of the co-delivery system group to HUVEC cells is within the range of 56-68%, which is higher than that of Dox group, PO-6+Dox group and M-Dox group.

Experiment 10: Effect of Polypeptide Complex on the Survival of AML1-ETO Mice The mice used in this experiment were 6-8-week old female C57 mice (from the Animal Experimental Center of the Institute of Basic Medical Sciences Chinese Academy of Medical Sciences), which were raised in an SPF level environment. $1\times10^6$ primary spleen cells (GFP labeled) of AML1-ETO mice were suspended with 200 L sodium ethylenediaminetetraacetate (EDTA) in PBS and injected into C57 mice irradiated with sublethal dose (450 cGy) via tail vein. On the 11th day after injection, blood was taken from the tail vein of mice, and the positive rate of peripheral blood leukemia cells detected by flow cytometry was higher than 10%, which confirmed that the mice had developed disease. The mice confirmed to have developed disease were used in this experiment. From the 12th day after transplantation, the following groups of drugs were injected via tail vein:

(1) Polypeptide complex C-1 in Table 2 (the weight ratio of polypeptide PO-6 to $mPEG_{2000}$-$PCL_{2000}$ was 1:15), which was 10 mg/kg by weight of the polypeptide (the corresponding dose of $mPEG_{2000}$-$PCL_{2000}$ is 150 mg/kg), was recorded as C-1 group;

(2) Aseptic PBS solution, as the control group, was recorded as Con group;

(3) $mPEG_{2000}$-$PCL_{2000}$ dissolved in sterile PBS solution, 150 mg/kg, was recorded as $mPEG_{2000}$-$PCL_{2000}$ group.

Figure 13:
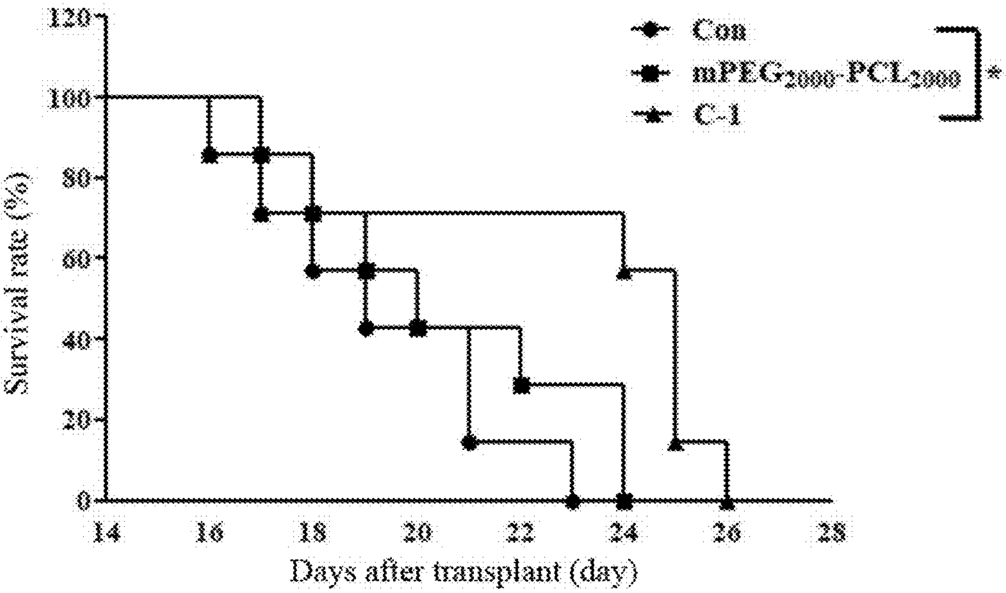
FIG. 13 shows the curve of polypeptide complex (C-1) of the invention prolonging the survival of AML1-ETO mice.

The drugs were administered every two days, and the results are shown in FIG. 13.

FIG. 13 shows that the median survival of mice in Con group is 19 days, that of mice in $mPEG_{2000}$-$PCL_{2000}$ group is 20 days, and that of mice in C-1 group is 25 days, which means that C-1 can significantly prolong the survival of AML1-ETO mice ($p<0.05$), indicating that the polypeptide complex has therapeutic effect on leukemia.

INDUSTRIAL APPLICABILITY

The polypeptide, polypeptide complex and co-delivery system provided in the invention has the function of targeting CD123-positive cells, can specifically bind to CD123-positive cells with high affinity, which provides a feasible treatment strategy for the treatment of leukemia and is suitable for industrial application.

What is claimed is:

1. An isolated polypeptide that specifically binds to a CD123 protein, wherein the polypeptide comprises an amino acid sequence selected from the group consisting of:

DDDYDTRAQGTDIGCDFRRISDDD (SEQ ID NO: 7)
and

GGDDDYDTRAQGTDIGNDFRRISDDD. (SEQ ID NO: 8)

2. The isolated polypeptide according to claim 1, wherein the amino acid sequence of the polypeptide is DDDYDTRAQGTDIGCDFRRISDDD (SEQ ID NO: 7) or GGDDDYDTRAQGTDIGNDFRRISDDD (SEQ ID NO: 8).

3. A polypeptide complex that specifically binds to a CD123 protein, wherein the polypeptide complex is prepared from raw materials including 1 pant by weight of the polypeptide of claim 1 and 1-50 parts by weight of a macromolecular material.

4. The polypeptide complex according to claim 3, wherein the average hydrodynamic diameter of the polypeptide complex is 50-150 nm.

5. The polypeptide complex according to claim 3, wherein the macromolecular material is selected from the group consisting of: a methoxy polyethylene glycol (mPEG)—polycaprolactone (PCL) (mPEG-PCL), a distearoyl phosphatidylethanolamine (DSPE)—polyethylene glycol 2000 (PEG2000) (DSPE-PEG2000), a polyvinyl caprolactam—polyvinyl acetate—polyethylene glycol, a polyoxyethylene polyoxypropylene ether block copolymer, a polylactic acid—glycolic acid copolymer, and combinations thereof.

6. The polypeptide complex according to claim 5, wherein the methoxy polyethylene glycol (mPEG)—polycaprolactone (PCL) is $mPEG_{2000}$-$PCL_{2000}$.

7. The polypeptide complex according to claim 5, wherein the macromolecular material is the polyoxyethylene polyoxypropylene ether block copolymer, and wherein the molecular weight ratio of polyoxyethylene to polyoxypropylene is 80:20, or wherein the macromolecular material is the polylactic acid—glycolic acid copolymer, and the molecular weight ratio of polylactic acid to glycolic acid is 50:50.

8. The polypeptide complex according to claim 5, wherein the macromolecular material is the polyvinyl caprolactam—polyvinyl acetate—polyethylene glycol, and wherein the molecular weight ratio of polyvinyl caprolactam, polyvinyl acetate and polyethylene glycol is 57:30:13.

9. The polypeptide complex according to claim 3, wherein the macromolecular material is a high polymer.

10. A method for preparing a polypeptide complex, the method comprising:

dissolving a macromolecular material and a polypeptide of claim 1 in PBS solution, and making them react at 25-75° C. for 20-120 min, so that the macromolecular material and the polypeptide form a complex, and placing the complex at room temperature until it is clear and transparent, and filtering to remove free polypeptides, to obtain the polypeptide complex, wherein the macromolecular material is selected from the group consisting of: a methoxy polyethylene glycol (mPEG)—polycaprolactone (PCL) (mPEG-PCL), a distearoyl phosphatidylethanolamine (DSPE)—polyethylene glycol 2000 (PEG2000) (DSPE-PEG2000), a polyvinyl caprolactam—polyvinyl acetate—polyethylene glycol, a polyoxyethylene polyoxypropylene ether block copolymer, a polylactic acid—glycolic acid copolymer, and combinations thereof.

11. The method according to claim 10, wherein the loading rate of polypeptide in the polypeptide complex is 50-100%.

12. The method according to claim 11, wherein the loading rate of polypeptide in the polypeptide complex is 60-100%.

13. A co-delivery system that specifically binds to a CD123 protein, wherein the co-delivery system is prepared by mixing components including the polypeptide complex of claim 3 and a chemotherapy drug; wherein the chemotherapy drug is selected from the group consisting of vincristine, doxorubicin hydrochloride, camptothecin, cyclophosphamide, and combinations thereof.

14. The co-delivery system according to claim 13, wherein the mass ratio of the chemotherapy drug to the polypeptide complex is from 1:10 to 1:80.

15. The co-delivery system according to claim 13, wherein the encapsulation rate of the chemotherapy drug in the co-delivery system is in the range of 30-99%.

16. The co-delivery system according to claim 15, wherein the encapsulation rate is 40-99%.

17. The co-delivery system according to claim 13, wherein the chemotherapy drug is doxorubicin hydrochloride.

18. A method for preparing a co-delivery system, wherein the method comprising, dissolving a chemotherapy drug in water to obtain a stock solution of the chemotherapy drug, wherein the chemotherapy drug is selected from the group consisting of vincristine, doxorubicin hydrochloride, camptothecin, and cyclophosphamide;

mixing the polypeptide complex of claim 3 with the stock solution of the chemotherapy drug at 25-75° C. for 20-120 min to form a mixture, and placing the mixture at room temperature, and filtering to remove free chemotherapy drug, to obtain the co-delivery system.

19. A method for treating a CD123-positive leukemia in a subject, the method comprising administering an effective amount of a polypeptide, a polypeptide complex, or a co-delivery system to the subject; wherein, the polypeptide comprises an amino acid sequence selected from the group consisting of:

```
                    (SEQ ID NO: 7)
DDDYDTRAQGTDIGCDFRRISDDD
and

                    (SEQ ID NO: 8)
GGDDDYDTRAQGTDIGNDFRRISDDD,
```

the polypeptide complex is prepared from raw materials including 1 part by weight of the polypeptide and 1-50 parts by weight of a macromolecular material, and the co-delivery system is prepared by mixing components including the polypeptide complex and a chemotherapy drug; wherein the chemotherapy drug is selected from the group consisting of vincristine, doxorubicin hydrochloride, camptothecin, cyclophosphamide, and combinations thereof.

20. The method according to claim 19, wherein the CD123-positive leukemia is selected from the group consisting of acute myeloid leukemia, acute lymphoid leukemia, and chronic lymphoid leukemia.

* * * * *

SEQUENCE LISTING

```
<160> NUMBER OF SEQ ID NOS: 9

<210> SEQ ID NO 1
<211> LENGTH: 22
<212> TYPE: PRT
<213> ORGANISM: Artificial Sequence
<220> FEATURE:
<223> OTHER INFORMATION: Polypeptide specifically binding to CD123
      protein
<220> FEATURE:
<221> NAME/KEY: Xaa
<222> LOCATION: (1)..(1)
<223> OTHER INFORMATION: Xaa is absent, or refers to Asp, Asp Asp or SEQ
      ID NO:2
<220> FEATURE:
<221> NAME/KEY: Xaa
<222> LOCATION: (7)..(7)
<223> OTHER INFORMATION: Xaa refers to Ala or Arg
<220> FEATURE:
<221> NAME/KEY: Xaa
<222> LOCATION: (12)..(12)
<223> OTHER INFORMATION: Xaa refers to Ile or Asp
<220> FEATURE:
<221> NAME/KEY: Xaa
<222> LOCATION: (14)..(14)
<223> OTHER INFORMATION: Xaa refers to Cys or Asn
<220> FEATURE:
<221> NAME/KEY: Xaa
<222> LOCATION: (22)..(22)
<223> OTHER INFORMATION: Xaa is absent, or refers to Asp, Asp Asp or Asp
      Arg Arg
```

```
<400> SEQUENCE: 1

Xaa Asp Tyr Asp Thr Arg Xaa Gln Gly Thr Asp Xaa Gly Xaa Asp Phe
1               5                   10                  15

Arg Arg Ile Ser Asp Xaa
            20


<210> SEQ ID NO 2
<211> LENGTH: 4
<212> TYPE: PRT
<213> ORGANISM: Artificial Sequence
<220> FEATURE:
<223> OTHER INFORMATION: Peptide

<400> SEQUENCE: 2

Gly Gly Asp Asp
1


<210> SEQ ID NO 3
<211> LENGTH: 20
<212> TYPE: PRT
<213> ORGANISM: Artificial Sequence
<220> FEATURE:
<223> OTHER INFORMATION: Polypeptide

<400> SEQUENCE: 3

Asp Tyr Asp Thr Arg Ala Gln Gly Thr Asp Ile Gly Cys Asp Phe Arg
1               5                   10                  15

Arg Ile Ser Asp
            20


<210> SEQ ID NO 4
<211> LENGTH: 20
<212> TYPE: PRT
<213> ORGANISM: Artificial Sequence
<220> FEATURE:
<223> OTHER INFORMATION: Polypeptide

<400> SEQUENCE: 4

Asp Tyr Asp Thr Arg Ala Gln Gly Thr Asp Asp Gly Cys Asp Phe Arg
1               5                   10                  15

Arg Ile Ser Asp
            20


<210> SEQ ID NO 5
<211> LENGTH: 21
<212> TYPE: PRT
<213> ORGANISM: Artificial Sequence
<220> FEATURE:
<223> OTHER INFORMATION: Polypeptide

<400> SEQUENCE: 5

Asp Tyr Asp Thr Arg Arg Gln Gly Thr Asp Asp Gly Cys Asp Phe Arg
1               5                   10                  15

Arg Ile Ser Asp Asp
            20


<210> SEQ ID NO 6
<211> LENGTH: 22
<212> TYPE: PRT
<213> ORGANISM: Artificial Sequence
<220> FEATURE:
<223> OTHER INFORMATION: Polypeptide

<400> SEQUENCE: 6
```

-continued

```
Asp Asp Tyr Asp Thr Arg Ala Gln Gly Thr Asp Ile Gly Cys Asp Phe
1               5                   10                  15

Arg Arg Ile Ser Asp Asp
            20


<210> SEQ ID NO 7
<211> LENGTH: 24
<212> TYPE: PRT
<213> ORGANISM: Artificial Sequence
<220> FEATURE:
<223> OTHER INFORMATION: Polypeptide

<400> SEQUENCE: 7

Asp Asp Asp Tyr Asp Thr Arg Ala Gln Gly Thr Asp Ile Gly Cys Asp
1               5                   10                  15

Phe Arg Arg Ile Ser Asp Asp Asp
            20


<210> SEQ ID NO 8
<211> LENGTH: 26
<212> TYPE: PRT
<213> ORGANISM: Artificial Sequence
<220> FEATURE:
<223> OTHER INFORMATION: Polypeptide

<400> SEQUENCE: 8

Gly Gly Asp Asp Asp Tyr Asp Thr Arg Ala Gln Gly Thr Asp Ile Gly
1               5                   10                  15

Asn Asp Phe Arg Arg Ile Ser Asp Asp Asp
            20                  25


<210> SEQ ID NO 9
<211> LENGTH: 23
<212> TYPE: PRT
<213> ORGANISM: Artificial Sequence
<220> FEATURE:
<223> OTHER INFORMATION: Polypeptide

<400> SEQUENCE: 9

Asp Tyr Asp Thr Arg Ala Gln Gly Thr Asp Ile Gly Cys Asp Phe Arg
1               5                   10                  15

Arg Ile Ser Asp Asp Arg Arg
            20
```